US005169388A

United States Patent [19]

McPhee

[11] Patent Number: 5,169,388

[45] Date of Patent: Dec. 8, 1992

[54] PRESSURE-ACTIVATED MEDICATION DISPENSER

[75] Inventor: Charles J. McPhee, Huntington Beach, Calif.

[73] Assignee: Gensia Pharmaceuticals, Inc., San Diego, Calif.

[21] Appl. No.: 535,396

[22] Filed: Jun. 7, 1990

[51] Int. Cl.[5] .................... A61B 19/00

[52] U.S. Cl. .................... 604/90; 604/89; 604/416; 604/403

[58] Field of Search .................... 604/403, 411, 412, 414, 604/415, 416, 89, 90, 91

[56] References Cited

U.S. PATENT DOCUMENTS

| | | | |
|---|---|---|---|
| 2,636,493 | 4/1953 | Lockhart | 604/90 |
| 2,649,090 | 8/1953 | Parsons et al. | 604/415 |
| 3,163,163 | 12/1964 | Wilburn | 604/90 X |
| 3,563,415 | 2/1971 | Ogle | 222/145 |
| 3,857,392 | 12/1974 | Ogle | 604/91 |
| 3,923,059 | 12/1975 | Ogle | 128/237 |
| 3,994,293 | 11/1976 | Ferro | 128/214 |
| 3,995,543 | 12/1976 | Lacey | 128/272 |
| 4,020,839 | 5/1977 | Klapp | 128/272 |
| 4,128,098 | 12/1978 | Bloom et al. | 128/272 |
| 4,191,225 | 3/1980 | Ogle | 141/329 |
| 4,194,640 | 3/1980 | Crankshaw et al. | 604/90 X |
| 4,203,443 | 5/1980 | Genese | 128/282 |
| 4,411,662 | 10/1983 | Pearson | 604/411 |
| 4,467,588 | 8/1984 | Carveth | 53/425 |
| 4,515,586 | 5/1985 | Mendenhall et al. | 604/89 X |
| 4,550,825 | 11/1985 | Sutryn et al. | 206/222 |
| 4,568,336 | 2/1986 | Cooper | 604/240 |
| 4,589,879 | 5/1986 | Pearson | 604/411 |
| 4,614,267 | 9/1986 | Larkin | 604/415 X |
| 4,675,020 | 6/1987 | McPhee | 604/411 |
| 4,781,679 | 11/1988 | Larkin | 604/88 |
| 4,871,354 | 10/1989 | Conn et al. | 604/89 |

FOREIGN PATENT DOCUMENTS 2105695 3/1983 United Kingdom .

OTHER PUBLICATIONS

Drawing (Attachment A labeled "Prior Art") of drug applicator sold by Burroughs Wellcome Co., Research Triangle Park, NC.

*Primary Examiner*—Robert A. Hafer
*Assistant Examiner*—Sam Rimell
*Attorney, Agent, or Firm*—Lyon & Lyon

[57] ABSTRACT

A drug dispenser comprising a drug vial to whose neck a hollow spike is attached for insertion into a diluent container, with a jaw around the spike grasping the inlet port of the container. A stopper seals the vial's throat, and a two-way value covers its mouth. The valve is opened, and the stopper is blown from the vial's throat by squeezing the diluent container, thereby sending diluent under pressure through the hollow spike, the open valve, and the unobstructed throat into the vial.

18 Claims, 4 Drawing Sheets

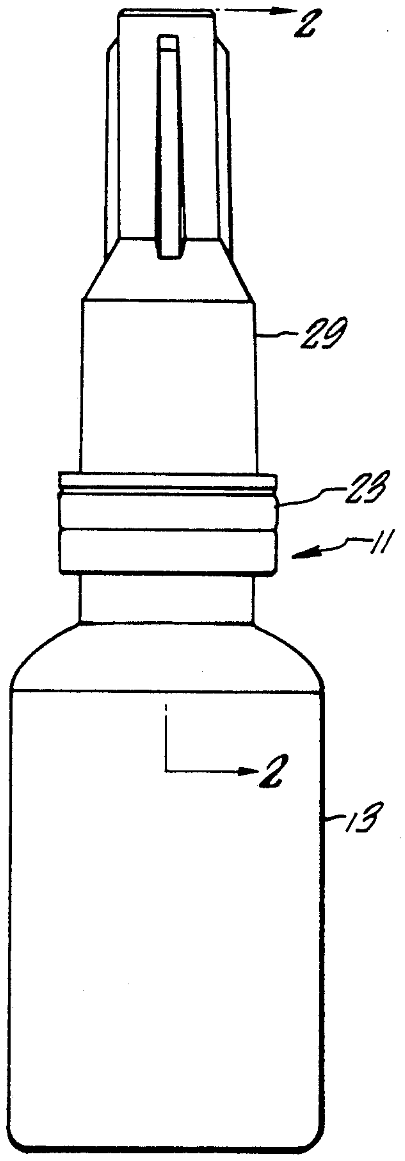
FIG. 1
FIG. 2
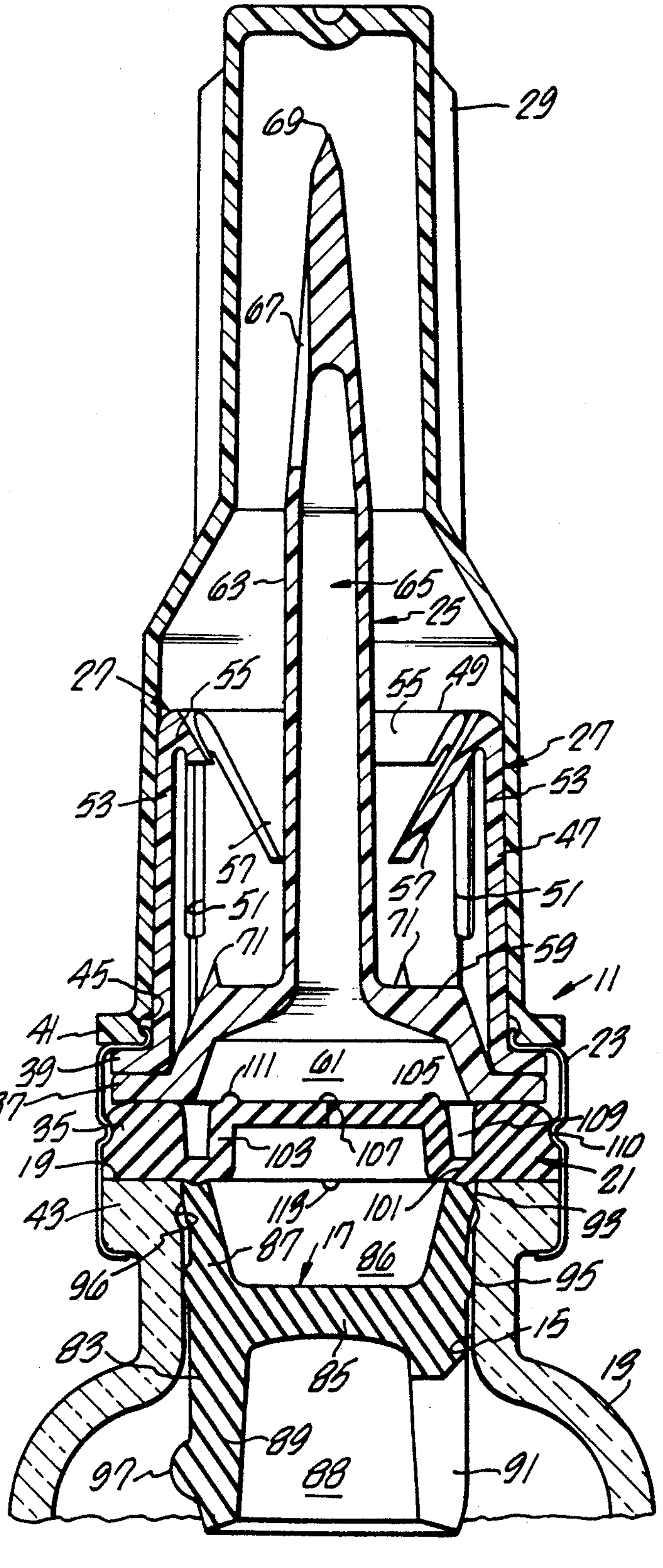

PRESSURE-ACTIVATED MEDICATION DISPENSER

FIELD OF THE INVENTION

The present invention relates to a spike-tipped drug dispenser whose contents may be transferred into a flexible-walled diluent container by jabbing the dispenser's spike through a pierceable stopper in the container's inlet.

BACKGROUND OF THE INVENTION

Medication that must be mixed with a diluent before being intravenously administered to a patient is conventionally packaged so that the medication is stored separately from the diluent. One way of so storing medication is to seal it in a drug vial while separately storing the diluent in a flexible-walled container. When the medication is to be mixed with the diluent, a connector having oppositely-extending, intercommunicating, hollow spikes is attached to inlets of the drug vial and the container, so that the spikes penetrate pierceable stoppers in the inlets of the drug vial and the container. A portion of the diluent is then injected from the container into the drug vial by manually compressing the container, and, by pumping the container, the medication is withdrawn, along with the injected diluent, from the drug vial into the container and mixed with the balance of the diluent therein.

An alternative approach to separately storing medication and a diluent until the two are mixed, is to pre-attach, at the time of manufacture, a drug-injecting spike to the sealed inlet of a drug-containing vial. Such a pre-packaged assembly will typically be stored in a pharmacy as part of a stock of such assemblies containing other medications. Also stocked in such a pharmacy are sealed containers wherein are stored diluents of different compositions and amounts. Such diluent containers are typically flat, rectangular, flexible-walled pouches having a pair of openings along one edge. One opening serves as an inlet port, through which a drug may be drawn into the container as described, and the other serves as an outlet port, through which diluent mixed with the drug may be administered to a patient.

Some time (possibly exceeding a day) before a drug is to be administered, a request is placed for that drug and for a container having therein a diluent of the appropriate composition and amount. In filling the order, the pharmacist selects the appropriate drug dispenser and diluent container, removes a protective cap which covers the dispenser's spike, and inserts the spike through the pierceable stopper in the container's inlet port. Both in the case of the drug vial/diluent container which are coupled through a separate, double-spiked connector, and in the case of the drug dispenser in which the drug vial and the drug-injecting spike are pre-assembled, it is necessary, after the drug vial has been connected to the diluent container, to keep the contents of the drug vial and the diluent container separate, until just before the drug is to be intravenously administered to a patient. This is so because, once the drug and the diluent are mixed, the mixture's life is limited to a few hours. Therefore, while it is desirable to have an order for a particular drug/diluent combination filled several hours, perhaps even a day or more, before the drug is to be administered, it is in most cases mandatory that they not be intermixed until shortly before administration.

The object of the present invention is to provide a mechanism whereby the contents of a drug dispenser of the type comprising a drug vial with a pre-attached diluent spike may be kept isolated from the contents of a diluent container even after the dispenser's spike has been inserted in the diluent container, and to readily free a passage between the drug vial and the diluent container when it is desired to mix their contents.

SUMMARY OF THE INVENTION

In accordance with the invention, there is provided a drug dispenser which may be sealingly connected to a pressurizable diluent container so as to transfer diluent between the container and the drug dispenser when the container is pressurized. The drug dispenser includes a drug vial having a stopper seated in and sealing its throat, and a normally-closed check valve which extends over the stopper and provides an additional seal across the vial's mouth. Means are provided for effecting pressurized communication between the container and the drug dispenser, the latter being characterized in that its valve can be opened and its stopper dislodged from its throat by pressurizing the container.

Preferably, the container includes a neck having a port sealed by a penetrable stopper and surrounded by a peripheral rim, and the means for effecting pressurized communication includes a spike for penetrating the stopper and a jaw member for latching the container port's rim. The spike has an axially-extending bore and at least one opening extending from the spike's bore through its wall. The jaw member is provided with a set of axially-extending, resilient arms that surround the spike and extend generally parallel therewith, terminating in teeth adapted to latch onto the peripheral rim surrounding the container's port when the spike is jabbed through the container's penetrable stopper.

The container is preferably a deformable bag, pressurizable by manual squeezing, and the drug dispenser's valve and stopper are so dimensioned that the valve opens, and the stopper is blown by a pressure which can be developed by manual squeezing of the container, preferably not more than 10 pounds per square inch. Optimally, a pressure which is less than that required to dislodge the stopper is sufficient to open the valve, so that it opens before the built-up pressure is sufficient to blow the stopper.

BRIEF DESCRIPTION OF THE DRAWINGS

These and other features and advantages of the invention will be more apparent from a reading of the claims and of the detailed description of the invention in conjunction with the drawings described below.

FIG. 1 is a side view of one exemplary embodiment of the drug dispenser of the present invention, with its protective cap covering its drug-dispensing spike;

FIG. 2 is a cross-section through the assembly of FIG. 1 along lines 2—2;

DETAILED DESCRIPTION

Figure 3:
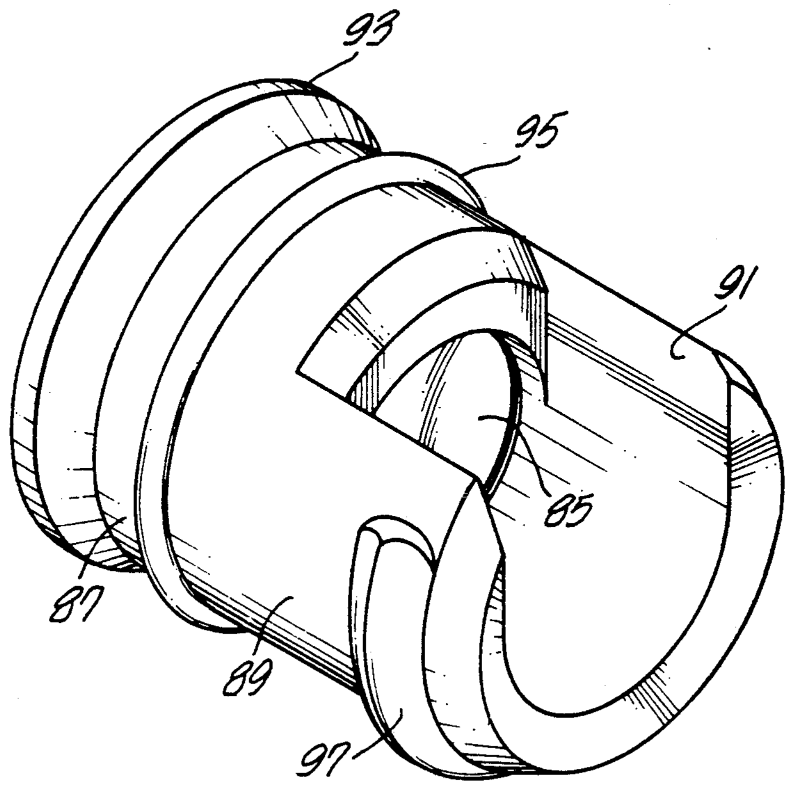
FIG. 3 is a perspective view of one exemplary embodiment of a rubber stopper constructed in accordance with the invention and fitting into the neck of the drug vial illustrated in FIGS. 1 and 2.
Figure 4:
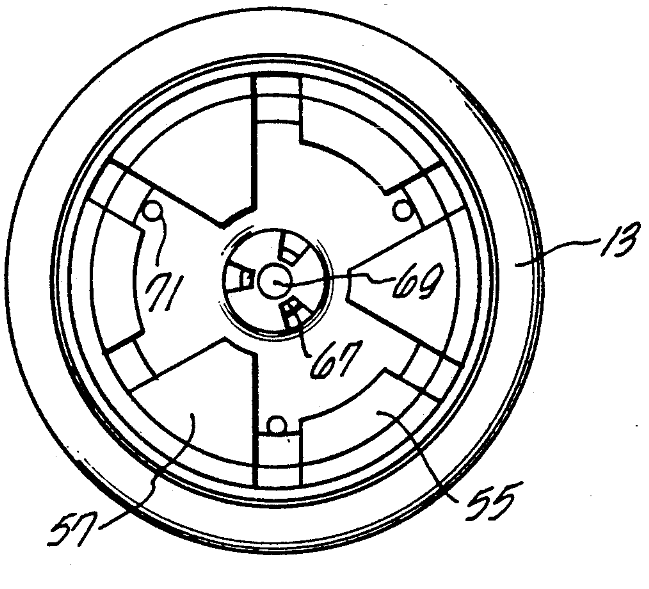
FIG. 4 is a top view of the assembly shown in FIG. 2, but with the protective cap removed to reveal the underlying structure.

An exemplary embodiment of a drug dispenser 11 incorporating features of the present invention is shown in FIGS. and 2. Its principal parts (referring particularly to FIG. 2) are a drug vial 13, having a throat 15 blocked by a stopper 17, and a mouth 19 covered by a disk-shaped check valve 21. Attached by a metal clip 23 to the mouth of the vial, are a spike member 25, for penetrating the pierceable stopper of a diluent container, and a jaw member 27 for attaching the drug dispenser 11 to the diluent container. Covering the foregoing assembly is a protective cap 29. The valve 21, spike member 25, jaw member 27, and protective cap 29, respectively, terminate in annular rims 35, 37, 39, and 41, which are stacked, in that order, upon the peripheral, annular rim 43 of the drug vial 13 by means of the metal clip 23. The rims 35, 37, and 39 are clamped within the generally-U-shaped channel formed by the retaining clip 23, causing the valve 21, spike member 25 and the jaw member 27 to be permanently attached to the drug vial 13. The peripheral rim of the protective cap 29, on the other hand, is removably held by the clip 23 through the expedient of an inner, circumferential groove 45 around the inner surface of the protective cap's rim 41. The upper rim of the clip 23 is outwardly curled to hook into the cap 29, snapping in place when the protective cap 29 is slid onto the jaw member 27.

The jaw member 27 serves to lock the drug dispenser 11 in place when the dispenser is engaged to a diluent container. It comprises a sleeve 47, which surrounds the base of the spike member 25 and is coaxial therewith. The sleeve 47 is split into a plurality of arms 53 by a set of evenly-distributed, axially-extending slots 51. Alternate ones of the arms 53 terminate in short reentrant teeth 55, while the remainder of the arms 51 terminate in long reentrant teeth 57, with both the short and the long teeth 55 and 57 extending diagonally inward from the arms toward the axis of the jaw member. The purpose and advantages of alternating arms with short and long teeth in a jaw member of the type described, and the manner in which they engage a container, will shortly become apparent with reference to FIGS. 5, 7A, and 7B.

Figure 5:
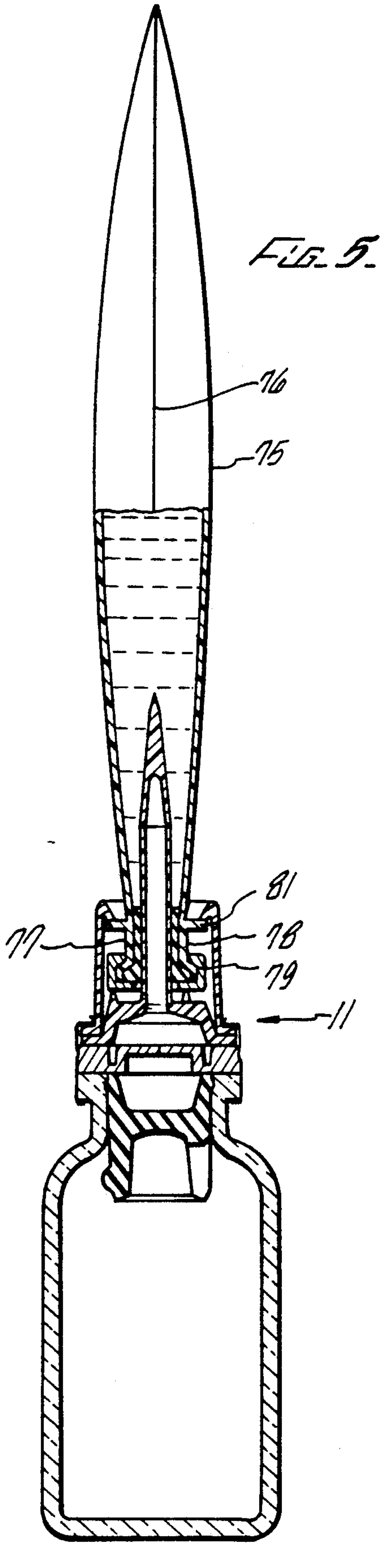
FIG. 5 is a cross-sectional view of the drug dispenser illustrated in FIG. 2 attached to a diluent container, with the spike of the dispenser extending into the diluent container and with the rubber stopper in place in the drug vial's neck.
Figure 6:
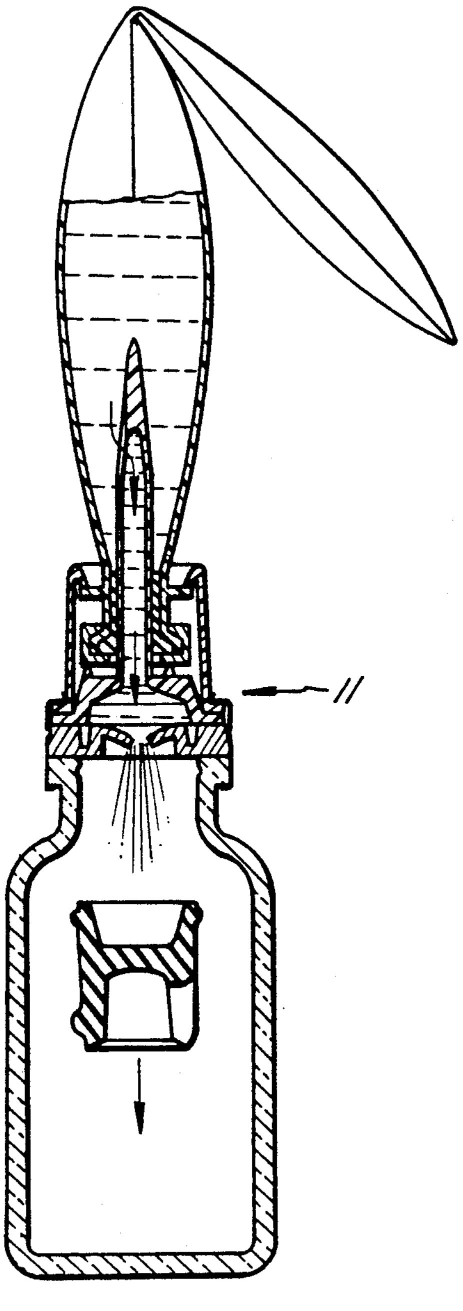
FIG. 6 shows the diluent container folded upon itself and squeezed, resulting in pressurizing the diluent until the stopper is dislodged from the drug vial's neck and blown into the drug vial.
Figure 7A:
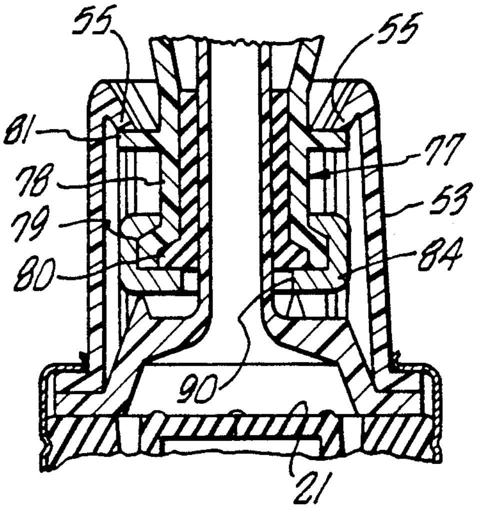
FIGS. 7A and 7B are enlarged views of a portion of FIG. 5, to show the manner in which the diluent container is engaged by the drug dispenser.
Figure 7B:
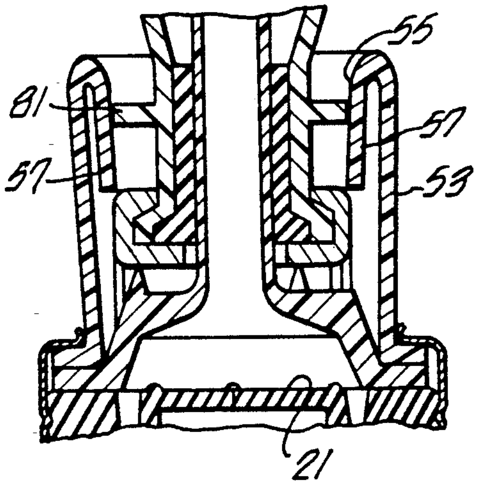

The spike member 25 comprises a spike 63 having an axial bore 65 communicating, near the spike's distal end or tip 69, with a set of three openings 67. At its proximal end the spike 63 terminates in a hollow, frustroconical pedestal 59 defining a dome-like chamber 61, from whose edge extends the peripheral rim 37, described previously. The chamber 61 communicates with the axial bore 65 of the spike 63. Extending from the roof of the pedestal 59, and distributed evenly around its outer edge, are three pointed extensions 71 which serve to aid in the engagement of the drug dispenser 11 with the diluent container. Such a container 75 is shown in FIGS. 5 and 6 and in some detail in FIGS. 7A and 7B. The container 75 is generally flat and rectangular, resembling in shape a hot-water bottle, but about a quarter of the size. It is shown edge-on, in end view, partially broken away, in FIGS. 5 and 6, with one of its edges 76 being partially visible and partially broken away. The container 75 is of conventional construction and includes a pair of ports, one of which, the inlet port 77, is shown in FIGS. 5, 6, 7A, and 7B. It includes a neck 78, surrounded by first and second collars 79 and 81. As is best seen in FIGS. 7A and 7B, a rubber stopper 80 is held in the container's neck 78 by an apertured, metal retaining cap 84. The drug dispenser 11 is initially engaged with the diluent container 75 by removing the dispenser's protective cap 29 and pressing the needle point 69 of the spike 63 through the aperture of the retaining cap 84 against the rubber plug 80, piercing it. The spike is pressed further into the container 75 until the set of short fingers 55 of the jaw member 27 have cleared the second collar 81 around the container's neck and have snapped in place around it. Because the axial spacing between the tips of the short and long teeth 55 and 57 is the same as that between the collars 81 and 79, at the same time that the short teeth 55 snap around the collar 81, the long teeth 57 will snap in place around the collar 79. At the same time, the pointed projections 71 at the spike's base press into the metal retaining cap 84. This completes engagement of the drug dispenser 11 and the container 75.

Figure 8:
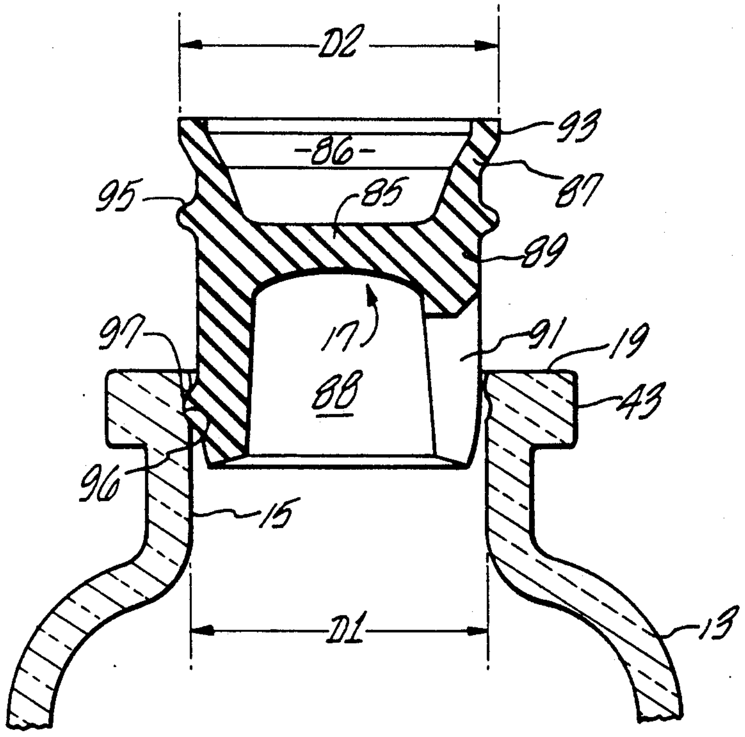
FIG. 8 is a cross-section showing the stopper in the drug vial's neck in an initial position, during which vapors may be vented from the drug vial during processing and prior to its being sealed.

In accordance with the invention, the valve 21 and the stopper 17 together provide a means whereby the contents of the drug vial 13 remain securely separated from the contents of the diluent container 75 until the diluent container is pressurized, at which time the valve 21 opens, and the stopper leaves the vial's throat 15 and is blown into the vial 13, as shown in FIG. 6. To help accomplish the above function, the stopper 17 is preferably constructed of an elastomer, such as butyl rubber, and, as is best seen in FIGS. 3 and 8, is in the shape of a cylinder having a transverse wall 85 intermediate its ends, and first and second cylindrical wall portions forming sealing skirts 87 and 89, extending in axially-opposite directions from the transverse wall 85. The first skirt 87 is tapered toward its distal end, for increased flexibility, and terminates in an outwardly-flared ridge 93. A second annular ridge 95 extends between the annular wall 85 and the flared ridge 93 around the periphery of the stopper. Referring to FIG. 2, the first skirt 87 forms an open chamber 86 facing toward the chamber 61, while the second skirt 89 forms a second open chamber 88 facing in the axially-opposite direction. Cut into the second skirt 89 is an axial slot 91, causing the chamber 88 to be open, not only at its end, but also along its side. A third annular ridge 97 extends around the perimeter of the distal end of the skirt 89.

In order to assist in understanding functions of the stopper's structural features, the manner in which the stopper 17 is first inserted into the drug vial 13, in the course of manufacture will be described next, with specific reference to FIG. 8. Medication may be sealed in the drug vial 13 in either liquid or powdered form. Where the medication is to be stored in powdered form, it may be placed in the vial 13 as a liquid suspension and heated until the liquid evaporates and only a drug powder residue remains. The latter method is known as "lyophilization." It is to accommodate this process that the axial slot 91 is cut in the skirt 89 of the stopper 17.

In particular, in the event that the drug dispenser 11 is to contain a powdered form of drug, its manufacture will include, as one of its initial steps, being partially filled with a liquid suspension of the drug, after which the stopper 17 is partly inserted into the drug vial's throat 15 until the bottom ridge 97 of the stopper seats in an annular groove 96 in the drug vial's rim 43. The drug vial 13 is then heated until its liquid contents are driven off through the axial slot 91 of them partly-inserted stopper 17. After the heating step is completed, the stopper 17 is pressed into the drug vial's neck 15 until the top of the stopper is flush with the mouth 19 of the drug vial 13 (the position shown in FIG. 2). In this position, the top two ridges 93 and 95 of the stopper 17 effect a sealing engagement with the neck 15 above and below the groove 96. It is apparent that the ridge 97, the chamber 88, and the slot 91 lend the stopper 17 a valve-like function through which the vial 13 is vented through the slot 91 when the stopper is in its upper (open) position (FIG. B) and is sealed when the stopper is in its lower (closed) position (FIG. 2).

It is desired that the pressure needed to dislodqe the stopper 17 be that which will be readily generated by manually squeezing diluent container 75, typically, no greater than 10 pounds per square inch. In order to ensure that the pressure required to dislodge the stopper 17 does not exceed a predetermined limit, such as 10 pounds per square inch in the example described herein, the diameter D2 of the stopper 17 relative to the diameter D1 of the vial throat 15 needs to be selected with some care. In a particular prototype which was constructed for a drug vial having a throat diameter D1 of ½-inch, the diameter D2 of the stopper 17, at its ridges 93, 95, and 97, was selected to be 0.540. This slight interference-fit coupled with the flexibility of the stopper 17 due to the tapered geometry of its skirt 87, resulted in its being readily dislodged under a pressure of less than 10 pounds per square inch, while serving satisfactorily to fulfill its primary function of preventing leaks from the drug vial 13. Consistency in the amount of pressure required to dislodge the stopper 17 is preferably enhanced by covering the surfaces of the stopper 17 with an anti-friction coating, which is normally done by the manufacturer of the stopper. A suitable such anti-friction coating is that used by the West Company of Phoenixville, Pa., and referred to by that company as Pur Coat TM. In addition, a layer of silicone may also be applied to further enhance sealing.

The check valve 21 serves a dual purpose. Primarily, it is provided because, without it, after the stopper 17 has been removed from the vial's throat 15, diluent would be free to flow from its container 75 back into the vial 13, when it is no longer desired to permit such flow to occur. To appreciate the importance of this factor, it needs to be understood that, after the drug dispenser 11 is attached to the diluent container 75, the following events occur: (1) the container 75 is folded back upon itself and squeezed, causing the valve 21 to open and the stopper 17 to leave the vial's throat 15, as shown in FIG. 6; (2) diluent leaves the container 75, along the path shown by arrows in FIG. 6, and flows through the interior of the spike 63, through the valve 21, into the vial 13; (3) the assembled vial and container 13, 75 are inverted, and the container 75 is repeatedly squeezed in a pumping action until all of the diluent, now mixed with the drug in the vial 13, has been withdrawn from the vial 13. Thereafter, the assembly is again inverted so that the vial is at the bottom, as shown in FIG. 5, and the assembly is suspended, with the vial hanging from the container. This is so that the diluent/drug mixture will flow under the force of gravity from a set port (not shown), which is located along the bottom edge of the container 75, adjacent to the inlet port 77. It is through that set port that the diluent/drug mixture is administered intravenously to a patient. It is apparent that means must be provided to prevent the diluent from re-entering the drug vial 13 when the assembled container/vial is suspended in the position shown in FIG. 5; otherwise, the diluent that flows into the bottle will remain there and will not be dispensed to the patient.

Referring particularly to FIG. 2, the check valve 21 is in the form of a disk, which may be of butyl rubber, like the stopper 17. Extending radially inward from the peripheral rim 35 of the valve is an annular ledge 101, from which there extends axially an annular wall 103, terminating in a membrane 105, extending radially inwardly from the axially-extending wall 103. A diametrically-extending slit 107 is cut in the membrane 105, permitting fluid to pass through the membrane, either from the diluent container 57 through the drug vial 13 or in the opposite direction, when diluent is withdrawn therefrom, back into the container 75. Preferably, the pressure required to open the valve 21 is less than that required to dislodge the stopper 17. Thus, in the prototype referred to earlier, the valve was constructed so as to open at between 3 and 5 pounds per square inch of pressure. Contributing to the forces tending to keep the valve closed, is the axial pressure exerted upon the valve rim 35 by the centrally-disposed, dimpled ridge 110 on the retaining clip 23. The amount of such pressure, however, is alleviated by the stress-relieving groove 109, formed by the rim 35, the annular ledge 101, and the axially-extending wall 103. A second purpose served by the check valve 21 is to provide a backup to the stopper 17 in sealing the throat 15 and mouth 19 of the vial 13. It has been found that such a dual seal significantly enhances the integrity of the seal beyond what could be achieved with the stopper 17 alone.

It may be seen from the foregoing that the drug dispenser of the present invention has unique advantages. Its sealing system, in particular, provides a convenient means for having the stopper in place in the vial during the lyophilization process, following which it can simply be pushed into place. Furthermore, the sealing system provides a secure seal for the vial's contents until it is ready to be used, at which time communication between the drug vial and a diluent container to which it has been attached can be accomplished simply by folding the container upon itself and squeezing until sufficient pressure is developed to open the valve and blow the stopper into the vial. Yet, by virtue of the backup function of the check valve 21, the diluent/drug mixture, once fully drawn into the diluent container, is prevented from leaking back into the drug vial, saving all of it for administration to the patient.

Individual features of the invention may find utility both in combination and separately from each other, and modifications to the structure may be made without departing from the scope of the invention, which shall be defined only by the claims.

What is claimed is:

1. A drug dispenser adapted to be sealingly connected to a pressurizable diluent container so as to transfer diluent between said container and said drug dispenser, comprising in combination:

(a) a drug vial having a neck and a throat within said neck;

(b) a stopper seated in and sealing said throat;

(c) a normally closed valve adjacent to and extending over said stopper and further sealing said throat; and (d) means for effecting pressurized communication between said container and said drug dispenser, said drug dispenser being characterized in that said valve can be opened and said stopper can be dislodged from said throat by pressurizing said container.

2. The drug dispenser of claim 1, wherein said stopper is covered with an anti-friction coating to minimize variation in the container pressure required to dislodge said stopper.

3. The drug dispenser of claim 1, wherein said stopper is formed of an elastomer.

4. The drug dispenser of claim 3, wherein said stopper is formed of butyl rubber.

5. The drug dispenser of claim 1, wherein the pressure required to dislodge said stopper is greater than that required to open said valve.

6. The drug dispenser of claim 5, wherein the pressure required to dislodge said stopper does not exceed 10 pounds per square inch.

7. The drug dispenser of claim 1, wherein said container is a deformable bag which is pressurizable by manual squeezing, and wherein the pressure required to dislodge said stopper does not exceed that which can be developed by squeezing said container.

8. The drug dispenser of claim 7, wherein said pressure does not exceed about 10 pounds per square inch.

9. A drug dispenser adapted to be sealingly connected to a pressurized diluent container so as to transfer diluent between said container and said drug dispenser, comprising in combination:

(a) a drug vial having a neck and a throat within said neck;

(b) a stopper comprising a hollow cylinder divided by a radially-extending wall into first and second cylindrical wall portions respectively defining first and second chambers open in axially-opposite directions and terminating in first and second rims respectively, seated in and sealing said throat;

(c) a normally closed valve extending over said stopper and further sealing said throat; and (d) means for effecting pressurized communication between said container and said drug dispenser, said drug dispenser being characterized in that said valve can be opened and said stopper can be dislodged from said throat by pressurizing said container.

10. The drug dispenser of claim 9, wherein the second of said chambers has an opening in its cylindrical wall portion extending axially from the rim of said second chamber towards said wall.

11. The drug dispenser of claim 10, wherein said first wall portion is outwardly flared so as to provide a sealing skirt for engaging said drug vial throat.

12. A drug dispenser adapted to be sealingly connected to a pressurizable diluent container which includes a neck having a port sealed by a penetratable stopper and surrounded by a peripheral rim, so as to transfer diluent between said container and said drug dispenser, comprising in combination;

(a) a drug vial having a neck and a throat within said neck;

(b) a stopper seated in and sealing said throat;

(c) a normally closed valve extending over said stopper and further sealing said throat;

(d) a spike having an axially-extending bore in at least one opening extending through the wall of said spike from said bore, said spike permitting pressurized communication between said container and said drug dispenser, and (e) a jaw member having a set of axially-extending resilient arms surrounding said spike and extending generally parallel therewith, said arms terminating in reentrant teeth adapted to latch onto said rim when said spike is jabbed through said penetratable stopper, said drug dispenser being characterized in that said valve can be opened and said stopper can be dislodged from said throat by pressurizing said container.

13. The drug dispenser of claim 12, wherein said container is a deformable bag which is pressurizable by squeezing, and wherein the pressure required to dislodge said plug can be developed by manual squeezing of said bag.

14. The drug dispenser of claim 13, wherein the pressure required to dislodge said plug does not exceed about 10 pounds per square inch.

15. The drug dispenser of claim 14, wherein the pressure required to open said valve is less than that required to dislodge said plug.

16. The drug dispenser of claim 15, wherein said valve is formed of a disk having a central member with a single diametrically-extending slit therein.

17. The drug dispenser of claim 15, wherein said drug vial, said valve, and spike, and said jaw member each includes a peripheral flange, wherein said flanges are stacked in the order of the drug vial, valve, spike and jaw, and are held rigidly fastened in their stacked positions by a retaining hoop which encircles all of them.

18. The drug dispenser of claim 17 additionally including a protective cap having a reduced-diameter tip for enclosing said spike, an enlarged-diameter base dimensioned to snugly fit around the outside of said jaw member, said protective cap having an inner circumferential groove extending around its base, and said hoop terminating in an outwardly-curling rim which snaps into said inner circumferential groove when said protective cap is fitted onto said jaw member.

* * * * *